United States Patent [19]

Khandkar et al.

[11] Patent Number: 5,269,902
[45] Date of Patent: Dec. 14, 1993

[54] ION-CONDUCTING MODULE HAVING AXIALLY-ARRANGED SOLID STATE ELECTROLYTE ELEMENTS

[75] Inventors: Ashok C. Khandkar, Salt Lake City; Singaravelu Elangovan, Sandy, both of Utah

[73] Assignee: Gas Research Institute, Inc., Chicago, Ill.

[21] Appl. No.: 932,759

[22] Filed: Aug. 20, 1992

[51] Int. Cl.$^5$ .............................................. G01N 27/26
[52] U.S. Cl. ......................................... 204/426; 429/39
[58] Field of Search ................ 204/421, 422, 423, 424, 204/425, 426, 427, 428, 429; 429/32, 38, 39, 94

[56] References Cited

U.S. PATENT DOCUMENTS

| | | | |
|---|---|---|---|
| 4,490,444 | 12/1984 | Isenberg | 429/32 |
| 4,510,212 | 4/1985 | Fraioli | 429/39 |
| 4,664,987 | 5/1987 | Isenberg | 429/38 |
| 4,791,035 | 12/1988 | Reichner | 429/31 |
| 4,824,742 | 4/1989 | Parry | 429/30 |
| 4,874,678 | 10/1989 | Reichner | 429/32 |
| 4,885,142 | 12/1989 | Suitor et al. | 423/219 |
| 5,045,413 | 9/1991 | Marianowski et al. | 429/39 |
| 5,077,148 | 12/1991 | Schora et al. | 429/39 |

*Primary Examiner*—John Niebling
*Assistant Examiner*—Bruce Bell
*Attorney, Agent, or Firm*—Trask, Britt & Rossa

[57] ABSTRACT

A module for an ion-conducting device includes a plurality of spaced-apart, solid state ion-conducting electrolyte elements arranged substantially radially around a central plenum. A plurality of longitudinal gas flow channels is sealed off from the central plenum by a plurality of seals, and extend longitudinally through the module in the spaces between every other adjacent pair of electrolyte elements. A plurality of transverse gas flow channels is in fluid communication with the central plenum, and extend generally radially outward from it through the spaces between every-other adjacent pair of electrolyte elements not constituting a longitudinal gas flow channel. Manifold plates having a plenum aperture and a plurality of gas apertures therein are disposed on either side of the radially arranged electrolyte elements, and sandwich the elements therebetween. A plurality of the modules may be juxtaposed in a modular assembly wherein the central plenums of adjacent modules are aligned and in register, and combine to form an extended central plenum, the transverse gas flow channels in each module extend generally radially from the extended central plenum, and the longitudinal gas flow channels of adjacent modules are aligned and in register and in fluid communication and form extended longitudinal gas flow channels.

11 Claims, 4 Drawing Sheets

ION-CONDUCTING MODULE HAVING AXIALLY-ARRANGED SOLID STATE ELECTROLYTE ELEMENTS

BACKGROUND OF THE INVENTION

1. Field

This application relates to arrangements for the solid state ion-conducting electrolyte elements in an ion-conducting device, and more particularly to modular arrangements for multi-element ion-conducting devices.

2. State of the Art

Solid state ion-conducting electrolyte elements are typically constructed from materials capable of conducting, or permitting passage of, specific ions through the element. Various electrolyte materials will allow specific ions of a certain size or type to pass through the element from one side to the other. Materials having this capability include ceramic metal oxides such as bismuth oxide and cerium oxide, polymeric electrolyte membranes, and immobilized molten electrolyte membranes. The membranes are more pliant than the metal oxides, but conduct ions in a similar manner. Zeolyte membranes having pore sizes allowing diffusion of certain sized molecules across the membrane are also used for specific ion conduction. Each type of metal oxide or membrane electrolyte finds use in a different ion-conducting application.

The electrolyte elements, especially the ceramic metal oxides, are often formed as flat plates having an electrically conductive material attached to one or both of the plate's flat surfaces. When the electrode material comes in contact with a gas containing the uncharged form of the ionic species, an electrochemical reaction occurs at the electrode to produce the specific ion. The liberated ion may then migrate through the electrolyte element.

Ion-conducting devices typically utilize a plurality of electrolyte elements arranged whereby each element is spaced apart from successive elements. The spaces allow reactant gases necessary for ion-conducting activity to flow between the electrolyte elements, and come in contact with the electrode material attached to the surface of each element.

Ion-conducting devices find use in a variety of applications including fuel cells, steam electrolyzers, oxygen concentrators, and other types of electrochemical reactors. When used in fuel cell applications, fuel gases such as $H_2$, $CH_4$ containing gases, synfuels, or light hydrocarbon fuel stocks, are directed to one face of the spaced-apart elements, and air is directed to the opposing face. When used as an oxygen concentrator, air is directed to one face of the elements, and pure molecular oxygen is collected from the opposite face. Other ion-conducting devices function in a similar manner, but may have structural modifications, and different reactant gas requirements.

As previously stated, reactant gases flowing between the spaced-apart electrolyte elements come in contact with, and react at, the electrode material attached to the surface of the elements. For example, at one electrode surface of a fuel cell, an electrochemical reaction occurs in which an ionic species, such as $O^{-2}$ from air, is produced and conducted across the thickness of the element to the other electrode surface where it reacts with the fuel gas to form water and $CO_2$. In a typical fuel cell, this electrochemical reaction may be illustrated by the following equations:

Air Side

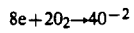

$$8e + 2O_2 \rightarrow 4O^{-2}$$

Fuel Side

$$CH_4 + 4O^{-2} \rightarrow CO_2 + 2H_2O + 8e$$

If the two electrodes on opposite faces of the electrolyte element are electrically connected in series, an electrical current may be obtained through passage of electrons between the two electrodes. This reaction occurs when the elements reach an operating temperature, typically 600°-1000° C. for ceramic oxide based fuel cells, and lower for polymer and molten electrolyte membranes. Energy released from the overall reaction contributes to maintaining the operating temperature. Conduction of the $O^{-2}$ ions through the electrolyte elements occurs due to a difference in the partial pressure of $O_2$ on opposite sides of the elements. In current based devices, an electrical potential may be applied across the elements to drive the reactions toward the product side.

An increase in the output from an ion-conducting device can be obtained by combining numerous elements into an assembly, and electrically connecting the elements in series or parallel. Parallel connection enables the device to continue functioning if an element fails, while series connection allows for increased voltage output from the device.

Fuel gases and air are typically supplied to the electrolyte elements of an assembly by a manifold. A gas supply manifold may be attached over the openings to the spaces between the elements so that reactant gases are directed between the elements. Similarly, a gas collection manifold may be attached to collect gases produced during operation of the device.

Each electrolyte element of an ion-conducting assembly must have access to reactant gases, which complicates manifolding of the device. If the elements are arranged adjacent to each other such as in a stack, a manifold can be attached to the side of the stack to direct reactant gases into the gas flow spaces between the elements. However, this arrangement is subject to several problems. The flow of gases between the elements becomes restricted as elements are added to the assembly, resulting in inefficient cooling in the downstream elements. Additionally, the downstream elements may receive fuel which has been partially depleted of the reactive species. The close packing of the elements, and reduced fuel and air flow, also interferes with maintaining the assembly at a uniform temperature, which further reduces the efficiency of the assembly. Additional elements also cannot be added to this type of arrangement without considerable difficulty, and construction of a new manifold.

Another option for supplying gases to, and collecting gases from, the elements is to manifold a group of electrolyte elements individually. This option allows the elements to be arranged in a pattern which facilitates uniform heating and gas flow, but makes for a bulky, and difficult-to-manufacture assembly. The increased number of seals between the manifold and the elements also increases the probability of a leak occurring in the gas supply or collection pathway. If a leak occurs in a fuel gas pathway, the fuel becomes diluted with air, which severely reduces its potential to participate in the electrochemical reaction on the fuel side of the electrolyte elements. If a leak occurs in a gas collection pathway, the pure gas from the ion-conducting activity may become contaminated with gases from the external environment.

Existing solid state ion-conducting electrolyte element and manifold arrangements also suffer from problems with oxidation of electrical pathway components. Because the electrical components are frequently exposed to the oxidizing environment of air, inexpensive electron-conducting materials, such as nickel, cannot be used due to their oxidative tendencies. This necessitates the use of expensive materials, such as silver or platinum, to avoid the oxidation which usually results in premature failure of the electrical pathway components.

SUMMARY OF THE INVENTION

The invention of the present application is a module having axially-arranged solid state electrolyte elements for use in an ion-conducting device. Each electrolyte element may be formed as a generally flat plate having a pair of opposed surfaces, and a thickness through which specific ions may be conducted. The electrolyte elements may be constructed from a solid state ion-permeable material such as a ceramic metal oxide, and may include an electrode material attached to one or both surfaces. The axial arrangement obviates many of the aforementioned problems with the arrangements of existing ion-conducting devices.

Each module includes a plurality of ion-conducting electrolyte elements axially arranged around a central axis, and radiating outward therefrom. The elements are disposed on edge, and spaced apart so that a plurality of gas flow passageways exists therebetween. A central plenum is defined in an interior area inward of the axially-arranged elements.

A plurality of longitudinal gas flow channels is disposed in the spaces between every-other of the spaced-apart elements. The inner peripheries of the longitudinal channels are sealed off from the central plenum by a plurality of plenum seals disposed between every-other element where the elements border the central plenum. The outer peripheries of the longitudinal channels are also sealed off with a plurality of perimeter seals so that a fluid pathway exists longitudinally through the thickness of the module via the longitudinal gas flow channels.

A plurality of transverse gas flow channels is disposed between the elements in the alternating spaces between every-other longitudinal gas flow channel. The transverse channels are in fluid communication with the central plenum and radiate outward therefrom. A cross flow geometry for the flow of gases through the module is thus facilitated by the longitudinal and transverse gas flow channels. A pair of manifold plates may be disposed above and below the electrolyte elements to sandwich the elements therebetween, and seal off the upper and lower edges of the transverse gas flow channels.

The axial arrangement of the module results in several significant advantages to the construction and operation of ion-conducting devices. The radial array of the electrolyte elements results in a higher pack of elements into a smaller space than is possible with conventional arrangements using stacks of parallel elements. The high packing density results in a higher ion-conducting capacity per unit volume, and thus a more efficient device can be constructed which occupies less space than conventional arrangements. The compact design also facilitates a thermally self-sustaining device due to the efficient configuration of the electrolyte elements.

The radial array of the electrolyte elements around a central axis also facilitates the use of compression seals between the elements where they border the central plenum. The compression seals provide for a much simpler manufacturing operation, and result in improved sealing efficiency between adjacent elements.

Manifolding the gas flow channels between the radial array of electrolyte elements is also much simpler, and more efficient than manifolding stacks of elements. The manifold plates which contact opposed edges of the elements to sandwich the elements therebetween can be used to manifold all the gas flow passageways in all elements in a module. In contrast, most manifold arrangements for stacks of elements require a separate manifold for each set of gas flow passageways through the stacks. In some arrangements, several sets of manifolds are required for sets of stacks.

The cross flow geometry of gases through the axially-arranged elements offers several advantages in supplying gases, especially fuel gases, to the elements, and in separation of products generated during operation. In operation as a fuel cell, fuel gases must be supplied to the elements in order to generate an electric current. If the fuel gas is allowed to mix with air and becomes diluted, the electrochemical reaction which is intended to occur on opposite sides of the elements, instead, occurs in the fuel gas channel. This results in loss of the chemical potential of the fuel gas consumed in the gas flow channel.

In the cross flow geometry of the instant invention, however, the seal between the manifold plates and the openings to the longitudinal gas flow channels is an efficient design, thereby reducing the likelihood of a leak developing in the longitudinal gas flow channels. The axial arrangement is also particularly convenient for use as a gas concentrator, especially an air-to-oxygen concentrator, because product gases such as oxygen, which accumulate on the product side of the elements may be collected from the central plenum, thereby reducing the likelihood of a leak occurring in the gas collection components. The cross flow geometry also results in fuel gas passageways which expand in cross sectional area from the central plenum outward, which minimizes the pressure drop along the length of the cells during combustion of fuel gases. Reduced pressure drop results in an increased volumetric flow radially outward along the cells, which helps to improve the efficiency of an ion-conducting device.

A plurality of modules may be juxtaposed into a modular assembly, wherein the number of modules can vary according to the requirements of a particular application. The modular design facilitates a flexibility in the construction of ion-conducting devices which is not available in many other arrangements.

A further understanding of the construction and operation of the axially-arranged ion-conducting module may be had from the following drawings and description of the illustrated embodiment.

DETAILED DESCRIPTION OF THE ILLUSTRATED EMBODIMENT

Figure 2:
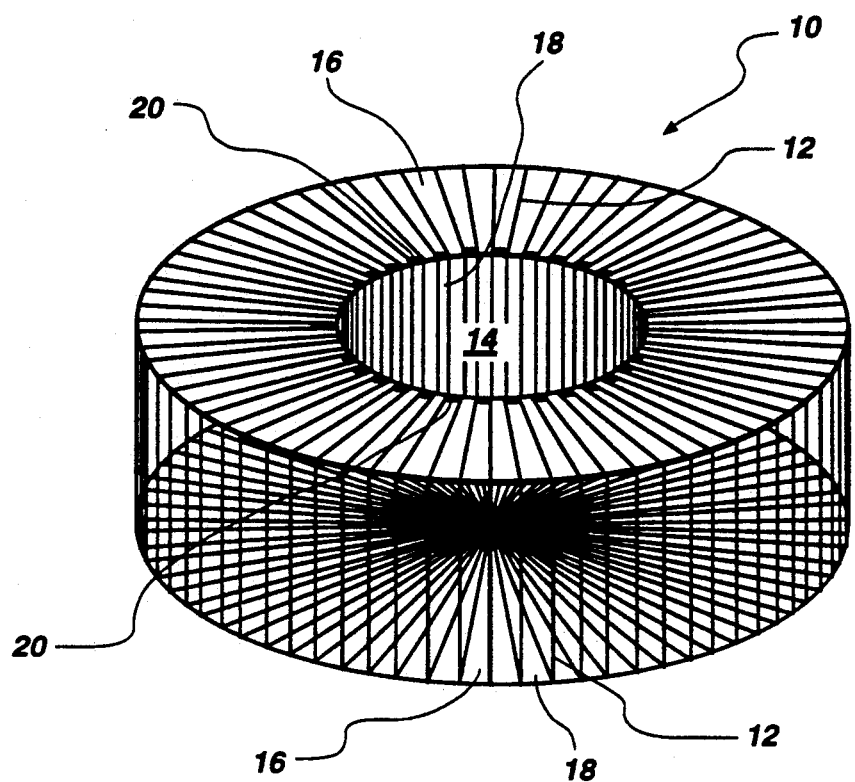
FIG. 2 is a perspective view of a portion of a module having axially-arranged electrolyte elements according to the instant invention.
Figure 3:
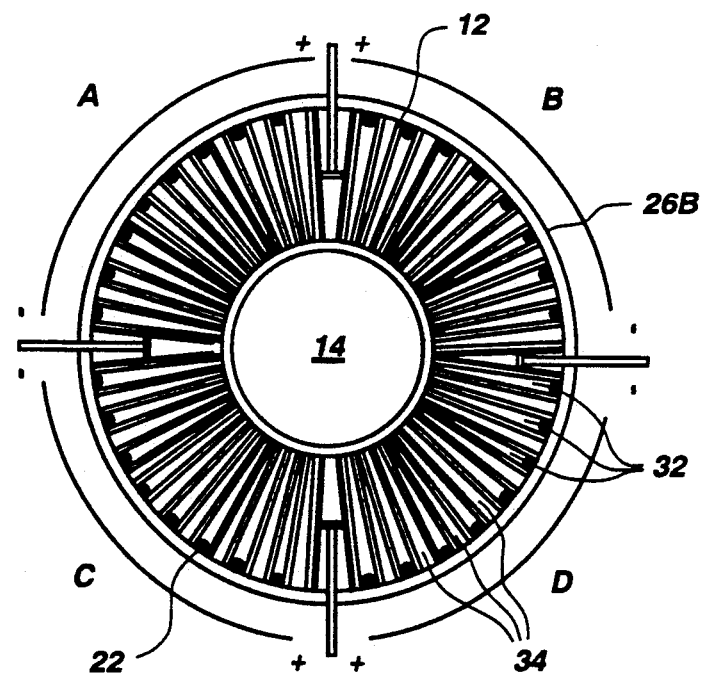
FIG. 3 is a plan view of the module in FIG. 2 illustrating the transverse gas flow channels and a possible electrical connection scheme for the electrolyte elements.

Referring to FIGS. 2 and 3, the module 10 of the instant invention includes a plurality of spaced-apart ion-conducting electrolyte elements 12 arranged on edge in a generally axial array around a central plenum 14. Although in the illustrated embodiment, the electrolyte elements 12 are in a circular arrangement, the elements may also be arranged in an oval around an oval shaped central plenum. Various numbers of electrolyte elements may be included in the module with perhaps 40 to 50 being typical.

A significant advantage to this arrangement is the high density packing of the elements into a relatively small area. The high density pack enables a more efficient ion-conducting device to be manufactured, which occupies less space than conventional stacked arrangements of parallel electrolyte elements. The close proximity of the electrolyte elements in the module also inclines the module towards thermally self-sustaining operation. There is less dead space in the module to heat, which results in efficient thermal convection, and reduces temperature differentials.

Figure 1:
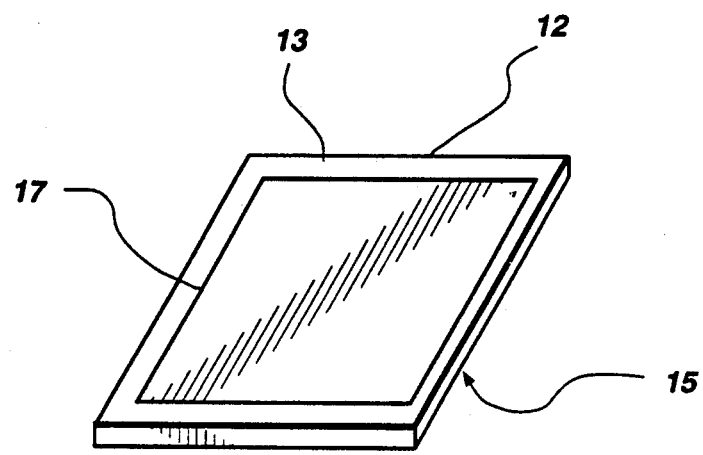
FIG. 1 is a perspective view of an ion-conducting electrolyte element which may be used in the module of the instant invention.

Referring to FIG. 1, the ion-conducting electrolyte elements 12 may be formed as generally flat plates having a pair of opposed flat surfaces 13 and 15, and a thickness through which specific ions may be conducted. The electrolyte plates may be constructed from solid state materials such as the ceramic metal oxides of zirconia, ceria, hafnia, and bismuth, or may be constructed from the more pliable polymeric electrolyte membranes and immobilized molten electrolyte membranes. An electrically-conductive electrode material 17 may be adherent to one or both flat surfaces of the plates to facilitate production of the ionic species from the reactant gas, and subsequent reformation into an electrochemical product on the opposite side of the electrolyte plates. Various applications for the module suggest or dictate the composition of the ion-conducting medium and the electrode.

Figure 6:
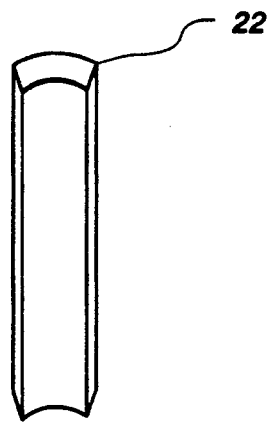
FIG. 6 is an elevational view of a plenum seal which fits between two adjacent electrolyte elements and seals off the longitudinal gas flow channels from the central plenum.

Referring again to FIGS. 2 and 3, a plurality of inter-element spaces 16 is disposed between adjacent plates. The spaces function as gas flow channels to enable reactant gases to flow between the plates. In a preferred arrangement, a plurality of primary plenum seals 18 is disposed in the spaces between every-other ion-conducting plate where the plates border the central plenum, to seal off every-other inter-element space from fluid communication with the central plenum 14. A plurality of secondary plenum seals 20 may be disposed outward of, and opposing the primary plenum seals, to further seal the inter-element spaces from the central plenum. FIG. 6 illustrates a primary or secondary plenum seal, the two seals being substantially similar except for a slight difference in size so as to fit within the expanding inter-element spaces 16. The plenum seals are in compression at the corners due to the axial arrangement of the elements, which improves the sealing capability and the reliability of the seals.

As best illustrated in FIG. 3, the inter-element spaces 16 which are sealed off from the central plenum 14 have a plurality of primary perimeter seals 22 disposed between the elements at the outer perimeter to seal off the outer perimeter of the intercellular spaces. In a manner similar to the secondary plenum seals 20, secondary perimeter seals 24 may be disposed inward of the primary perimeter seals to assure a gas-tight seal around the outer perimeter of the elements. The seal illustrated in FIG. 6 may also be employed as a perimeter seal, again after a slight size modification to accommodate the expanding inter-element spaces. As best illustrated in FIGS. 3 and 4, these sealed inter-element spaces form a plurality of longitudinal gas flow channels 32, the direction of flow through which is denoted by the solid vertical arrows in FIG. 4.

Figure 4:
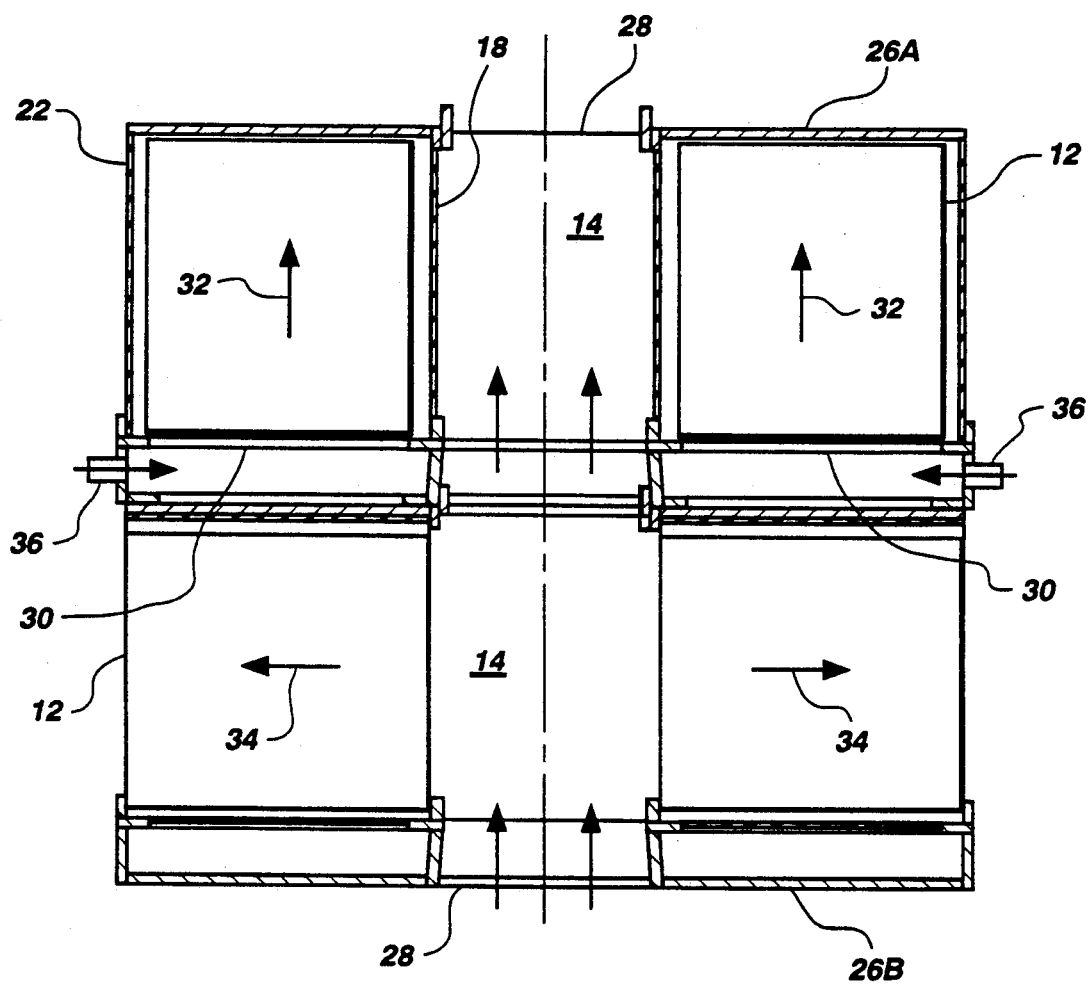
FIG. 4 is a cross sectional view through the center of two modules stacked one above the other in a modular assembly, and illustrating a possible directional flow of gases through the longitudinal and transverse gas flow channels.
Figure 5:
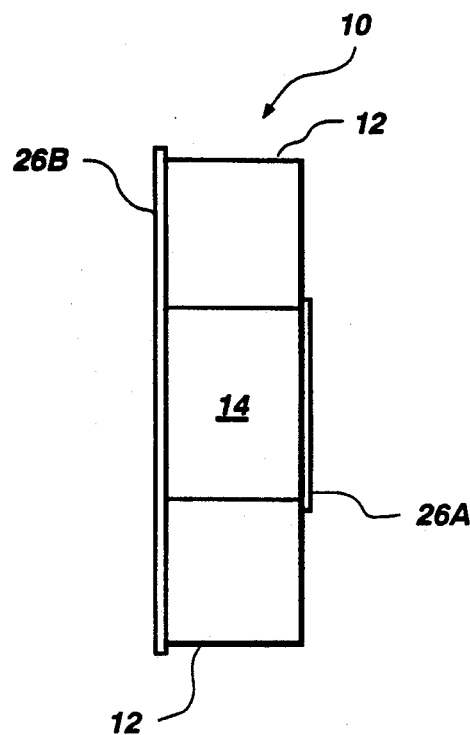
FIG. 5 is an elevational view of the module in FIG. 2.
Figure 7:
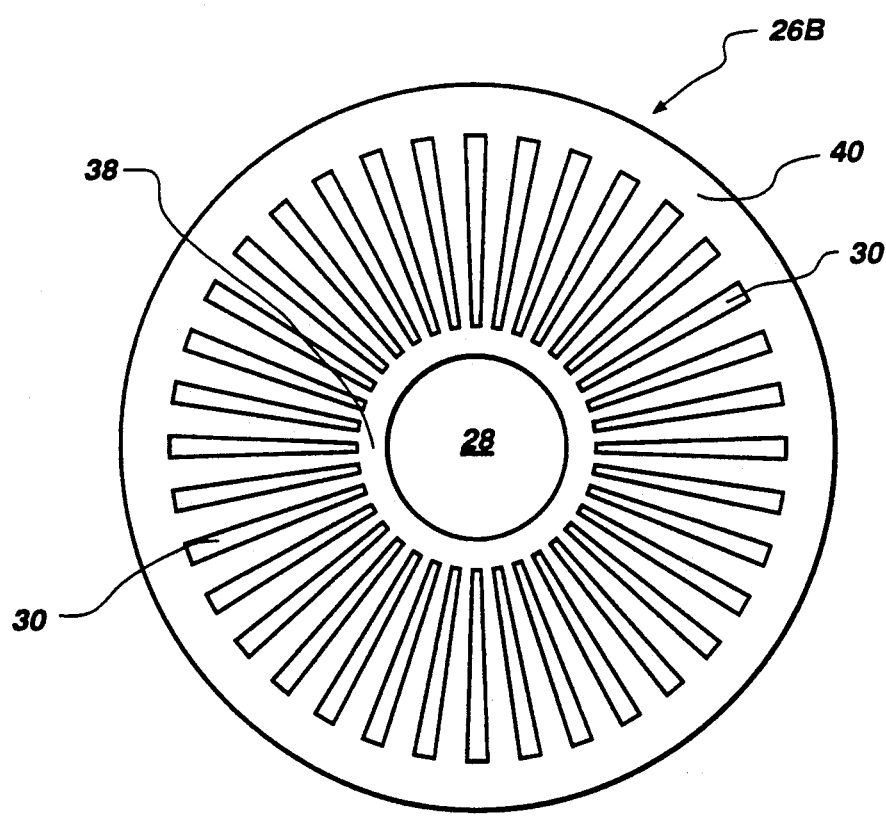
FIG. 7 is a plan view of a manifold plate.

Referring to FIGS. 4, 5, and 7, a pair of manifold plates 26A and 26B are disposed on either side of the axially-arranged plates 12, and sandwich the plates therebetween (i.e. the manifold plates seal opposed edges of the electrolyte elements). The manifold plates have a plenum aperture 28 therein which is in fluid communication with the central plenum 14. The manifold plates also have a plurality of longitudinal gas channel apertures 30 therein, which are in fluid communication with the longitudinal gas flow channels 32 between the plates. As best illustrated in FIG. 7, an inner margin 38 is disposed around the rim of plenum aperture 28 to provide a flat surface against which the manifold plate may seal against the edges of the electrolyte plates. Similarly, an outer margin 40 is disposed around the outer periphery of the manifold plate for the same purpose.

Referring again to FIGS. 3 and 4, the direction of gas flow through the longitudinal channels 32 is along the axis of the central plenum as indicated by the solid vertical arrows in FIG. 4. Gases entering these longitudinal channels through longitudinal gas channel apertures 30 flow through the thickness of the module.

As best illustrated in FIG. 3, a plurality of transverse gas flow channels 34 is disposed between the electrolyte elements and alternate with successive longitudinal gas flow channels 32. The transverse channels 34 are in fluid communication with the central plenum 14, and radiate outward from it to provide a radial flow pattern of gas (fuel gas preferably) between the individual elements of the module. The manifold plates 26A and 26B seal against the upper and lower edges of the transverse channels, and confine the gas flow through the channels in the direction indicated by the hollow horizontal arrows in FIG. 4. If a reactant gas, e.g. fuel, is supplied to the central plenum as indicated by the hollow vertical arrows in FIG. 4, the direction of gas flow is thus radially outward from the plenum through the transverse gas flow channels 34.

This pattern of gas flow may be referred to as a crossflow geometry, and results in several significant advantages to the construction and operation of an ion-conducting device. First, as illustrated in FIG. 4, the geometry enables modules to be juxtaposed together into a modular assembly, whereby the longitudinal gas flow channels 32 of adjacent modules are aligned and in register so that the longitudinal gas flow channels of each module are in fluid communication, and form extended longitudinal gas flow channels. Likewise, the central plenums 14 of adjacent modules are aligned and in register and form an extended central plenum. The transverse gas flow channels 34 of all the modules are thus in fluid communication with the extended central plenum of the modular assembly. A single manifold plate separates successive modules in the modular assembly illustrated in FIG. 4. In the modular assembly, the cumulative output from a plurality of modules may be obtained from one relatively compact assembly.

In the modular assembly illustrated in FIG. 4, the manifold plates separating successive modules may be identical in structure, while the manifold plates at the ends of the stack may be adapted to attach to a reactant gas supply or a product gas collection container. Other multiple module geometries for modular assemblies, such as a hexagonal closed-pack symmetry, are also feasible with the module.

When a fuel gas is introduced into the central plenum 14, the radial geometry results in fuel gas passageways which expand in cross sectional area from the central plenum outward. The expanding area minimizes the pressure drop along the length of the electrolyte elements during combustion of fuel gases which results in an increased volumetric flow radially outward along the elements. The result of the increased gas flow is improved efficiency in the ion-conducting device.

Referring again to FIG. 3, the electrolyte elements of the module may be electrically connected, for example, to harness the flow of electrons between the electrodes when the module is used as a fuel cell. The electrical connection scheme illustrated by the positive and negative symbols in FIG. 2 is a combination series and parallel connection arrangement wherein groups of electrolyte elements are divided into quadrants indicated as A, B, C, and D. Each electrolyte element in a quadrant is electrically connected in series, while adjacent quadrants are electrically connected in parallel. This electrical connection scheme enables the cumulative voltage output from the series-connected elements to be collected, while preventing loss of output from the entire module if one element or quadrant fails.

In a preferred operational configuration for a fuel cell application, a fuel gas is introduced into the central plenum 14 through the plenum aperture 28 in the manifold plate of the end module by a gas manifold attached to the end module of the modular assembly. The fuel gas flows through the central plenum 14 and radially outward between the electrolyte elements through the transverse gas flow channels 34. Air is introduced into the longitudinal gas flow channels 32 through the longitudinal gas channel apertures 30 in the end plate by an air manifold attached to one of the end plates. In an alternate embodiment illustrated in FIG. 4, reactant gases may be supplied to the longitudinal channels 32 by a plurality of nipples 36 attached between successive modules.

Electrically conductive bus bars for transporting the electrical current generated by a fuel cell may be disposed within the reducing atmosphere of the fuel gas channel, thereby obviating the need for expensive oxidation-resistant electrically conductive materials. Reliability is thus improved by reducing the likelihood of failure of the electrical pathway due to oxidation of the pathway components.

Other operational gas flow patterns may also be used in accordance with different applications. For example, when the modules are used in an oxygen concentrator, air may be introduced into the longitudinal gas flow passageways, and the pure oxygen from ion-conducting activity in all of the modules may be collected from the central plenum.

Although the invention has been described with a certain degree of particularity in structure, reference herein to details of the illustrated embodiment has been made by way of example only, and numerous changes in structural details may be resorted to without departing from the scope of the following claims.

What is claimed is:

1. A module for the electrolyte elements of an ion-conducting device comprising:

an axially oriented central plenum;

a plurality of flat, spaced-apart ion-conducting electrolyte elements, oriented on edge and arranged axially around, and substantially radiating from, said central plenum;

a plurality of spaces between said spaced-apart electrolyte elements;

a plurality of plenum seals disposed between every-other of said spaced-apart electrolyte elements where said elements border on the perimeter of said central plenum, said plenum seals sealing the joints between every-other of said elements at an inner periphery of said elements, and sealing said spaces between every-other of said elements from said central plenum;

a plurality of perimeter seals disposed between every-other of said spaced-apart ion-conducting elements outward of said plenum seals and at an outer perimeter of said axially-arranged electrolyte elements, said perimeter seals sealing the joints between every-other of said elements at the outer periphery of said elements, said plenum seals and said perimeter seals comprising the end walls of a plurality of longitudinal gas flow channels extending longitudinally through said module;

a pair of manifold plates disposed on either side of said axially-arranged electrolyte elements and sandwiching said elements therebetween, said manifold plates having a plenum aperture therein in fluid communication and in register with said central plenum, and having a plurality of longitudinal channel apertures therein in fluid communication with said longitudinal gas flow channels;

a plurality of transverse gas flow channels alternately disposed in said spaces between said electrolyte elements not comprising said longitudinal gas flow channels, said transverse gas flow channels in fluid communication with said central plenum and extending outward in a generally radial pattern from said central plenum; and means for electrically connecting said electrolyte elements in electrical series or parallel.

2. The combination of modules in claim 1 wherein a plurality of said modules are stacked juxtaposed together into a modular assembly wherein a manifold plate separates successive of said modules, said longitudinal gas flow channels of successive modules are aligned and in register and in fluid communication, said central plenum of adjacent modules are aligned and in register and in fluid communication, said central plenum of each of said modules forming an extended central plenum axially oriented through said modular assembly, and said transverse gas flow channels of each of said modules are in fluid communication with said extended central plenum, said modular assembly being bonded into a rigid structure.

3. The module in claim 1 wherein said electrolyte elements are arranged in a substantially oval configuration around said central plenum, and said central plenum is oval in shape.

4. The module in claim 1 wherein said electrolyte elements are constructed from a ceramic metal oxide.

5. The module in claim 1 wherein said electrolyte elements are constructed from polymeric electrolyte membranes.

6. The module in claim 1 wherein said electrolyte elements are constructed from immobilized molten electrolyte membranes.

7. The modular assembly in claim 2 wherein said electrolyte elements in each of said modules are separated from said electrolyte elements in adjacent modules by one of said manifold plates.

8. The module in claim 1 wherein said electrolyte elements are divided into an even number of groups, said elements within said groups being electrically connected in series, and said groups being electrically connected in parallel.

9. The module in claim 1 wherein a manifold for supplying reactant gases is connected to said module.

10. The module in claim 1 wherein a manifold for collecting gases produced during operation is connected to said module.

11. The combination of modules in claim 2 wherein a plurality of said modules are stacked juxtaposed into a modular assembly having hexagonal closed-pack symmetry, said plurality of modules being electrically connected.

* * * * *